United States Patent [19]

Camano

[11] Patent Number: 5,635,184

[45] Date of Patent: *Jun. 3, 1997

[54] ESSENTIAL OIL COMPOSITION WITH BACTERICIDE ACTIVITY

[75] Inventor: Ricardo M. Camano, Montevideo, Uruguay

[73] Assignees: Eduardo Haim Pinto; Teodoro Poradosu Haidenvurcel, both of Montevideo, Uruguay

[*] Notice: The term of this patent shall not extend beyond the expiration date of Pat. No. 5,512,284.

[21] Appl. No.: 254,009

[22] Filed: Jun. 3, 1994

Related U.S. Application Data

[63] Continuation-in-part of Ser. No. 75,117, Jun. 10, 1993, Pat. No. 5,512,284.

[51] Int. Cl.$^6$ .......................... A61K 35/78; A61K 31/05; A61K 31/01; A61K 47/00

[52] U.S. Cl. .......................... 424/195.1; 424/405; 514/731; 514/762; 514/783

[58] Field of Search .......................... 514/731, 762, 514/783; 424/195.1, 405

[56] References Cited

U.S. PATENT DOCUMENTS

| 4,963,356 | 10/1990 | Calenoff et al. | 424/91 |
| 5,110,594 | 5/1992 | Morita | 424/405 |

OTHER PUBLICATIONS

Chemical Abstracts, 106(26) 219349, 1987.
A Handbook of Mexican Roadside Flora, Charles T. Mason, Jr. et al., The University of Arizona Press, 1987, pp. 52–57.

*Primary Examiner*—John W. Rollins
*Attorney, Agent, or Firm*—Keck, Mahin & Cate

[57] ABSTRACT

The present invention relates with a bacterial composition comprising an effective amount of an essential oil distilled from a resinous tree preferably *Schinus Molle L*. *Pseudomonas aeruginosa* and *Staphylococcus aureus* are killed by the composition.

10 Claims, No Drawings

ESSENTIAL OIL COMPOSITION WITH BACTERICIDE ACTIVITY

This appln. is a CIP of application Ser. No. 08/075,117, filed Jun. 10, 1993, now U.S. Pat. No. 5,512,284.

The present invention is related with a composition that contains essential oil bactericide activity of the type of an essential oil distilled from a resinous tree, of the *Schinus Molle L.* species in a novel appropriate pharmaceutical dilution.

It arises from the microbiological analysis and the bactericide activity determination. The pharmacodynamic properties of this drug have a natural source and also have a topic application. Both characteristics are very important in those cases where resistance or intolerance to the systematic antimicrobial drugs exists.

It is known from U.S. patent application Ser. No. 08/075117 an essential oil composition having bactericidal activity comprising α-phellandrene, β-phellandrene, carvacrol, α- pinene and 13-pinene.

It has been now determinated that the combination of the above compounds and further compounds improves bactericidal activity. The additional components are canfene, sabinene, 1,8-cyneol: γ-terpinene, p-cimene and cariophylene.

Sabinene appears to have high importance in the composition's activity of the present invention.

The Sabinene is a $C_{10}H_{16}$ monoterpene bicycle. Its dextro isomers can be located in the essence of various species. The levo isomer and the racemic are not common in the nature. There are not known its crystalline derivatives. According to its origin, its physico-chemical constants are different, but the averages are B.p. 163/165, D 20 0.842, n 20 1.465, [α] D+80.2 It is easily to convert it to 4-terpineol to 1–4 terpine. Sabinene's formula can be represented

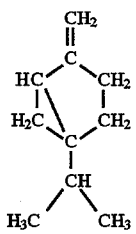

In the present case, the pathogenic microorganisms:
a) *Pseudomonas aeruginosa*
b) *Staphylococcus aureus* and
c) *Estreptococo* are killed by the drug, avoiding their development ability. Hence the fact that this drug has a principal roll in the wounds cleaning, reduction and elimination of the bacterial contamination.

A quick beginning of the bactericide action and a continuous activity are fundamental characteristics of the drug. Its liposolubilily and capacity of dispersion are very important because they make the introduction into the protoplasm and microorganisms easier. These characteristics are very important when this drug is used in surgical wounded patients, avoiding or even eliminating the terrible post-operative shock by *Pseudomona acruginosa* fit which is not controlled in all the hospitals of the world. The bactericide action depends on the following factors:
a) Concentration,
b) Temperature and pH,
c) Vehicle of drug application and
d) Time The time is an important factor, but is generally omitted or has not the appropriate pharmacokinetics importance, especially in those cases where time is a critical factor. Accordingly to Schmiedeberg, the pharmacodynamics actions should be the functional expression of the chemical nature reactions produced in the cellular plasmas by influence of the administered medicines.

Nowadays, chemistry cannot explain all the phenomena of the medicinal action. The effects of these drugs should be explained by the presence of determinate atomic groups characterized in their molecule. For example, any substance that has the KETONEQUINONE-C6 02-group, that it is to say aloes, rhubarb, cascara sagrada, etc., is laxative. It is certain that the pharmacodynamics action of the drug is not submitted to an only physic and chemistry law.

The drug of the present invention was obtained from the distillation, at reduced pressure, of the leaves and soft branches of the *Schinus Molle L.* species, of the Anacardiaceae family.

The present drug is an essential oil, obtained from the leaves and young branches of said plant. The essential oils are technically natural substances, very heterogeneous, which have vegetal sources and complex composition; and the are also one of the active properties of the plants.

According to the "World Health Organization" (WHO), a medicinal plant is "that one which contains active substances in one or more than one of their organs and that can be used with therapeutic purpose or can be precursors of the chemistry-pharmaceutical semisynthesis process".

The word drug is used here from the point of view of Medical Botanical, pharmacognosy, as all vegetal source substance or a mixture of them, administered in its natural state of further manipulation with an exclusively therapeutical action purpose. The *Schinus Molle L.* species which belong to the botanical Anacardiaceae family (from the Greek ANA=above, CARDIA=core).

It is a resinous tree, which has a medium to high size, reaching 8–10 meters high in its adult age; and a thick trunk with hard and slightly furrowed bark, with a round somewhat foggy treetop, without thorns, large, with hanging branches of perennial, not dense and light green foliage.

It has glabrous, pinnatifid leaves of about 35 cm long, in 25–45 sessile folioles, dentate, complete or darkly spaced dentate, from 1 to 5 cm long and 2 to 5 mm wide, petiole from 2 to 4 cm and slightly winged stalk.

The tree flowers are generally disposed in terminal bunches, from 10 to 20 long, in peduncles from 1,5 to 2 mm, calyx of 1 mm, glabrous, corolla with oblong petals longer than the calyx.

Its fruit is globe-shaped of about 4–5 mm of diameter and with a reddish epicarp. In regard to the phytogeographical situation, the *Schinus Molle L.* belongs to the botanical Uruguayan zone that comprises the territories of Uruguay, Mesopotamia and the west of Argentina, Paraguay and Bolivia.

It is usually found in Peru, central America and in North America, specially in the State of California, where it grows well and it is planted because of its elegant and beautiful appearance.

The method used for its essential oil (drug) extraction, allows the isolation with a good yield, working with large quantities of material, and carrying out a steam distillation at reduced pressure, where the steam is produced in other vessel or boiler. In case that the process should be hastened it is convenient to combine the wet steam with dry steam to make the hydrodiffusion easier.

In the industry the mills that can be used are SCHIMMEL, OTTO, DEROY, or EGROT. It is possible that aromatic distilled waters of the Schinus Molle L. as an industrial subproduct have an active participation in the fields of the medical cosmetology, pharmacy, drug trade, and aerosols manufacture.

The doses of drug, which has bactericide activity in vitro against *Pseudomona aeruginosa* and *Staphylococcus aureus* strains (according to the microbiologyc analysis of the Beltrán-Zunino Laboratory, Montevideo), was prepared using alcohol at 95° C. as vehicle, according to:

| | |
|---|---|
| -Essential oil of Schinus Molle L. (drug) | 1 gr. |
| -Alcohol at 95° C. (vehicle) | 100 cc. |

It is necessary to clarify that the above mentioned bactericide action is not due to the pharmacological kinetic and the chart of clinical status, all the vehicles, which are compatible with the pharmacognosy, pharmacodynamics, physiological, chemistry and dynamometric techniques principles, can be used in the formula.

Examples, the differences whereon the Pseudomona aeruginosa is found in the ear and in surgical wounds.

In regard to the factors that determine the susceptibility and the resistance of the microorganisms, the positive therapeutical results is the one whereon the drug dosis is enough to eradicate the microorganisms without causing toxicity in human cells. There were no signs of toxicity in the test that were carried out and because of this the overkill scope of the drug is quite extensive.

The identified components of the *Schinus Molle L.* essential oil are: α-phellandrene, β-phellandrene, carvacrol, α-pinene and β-pinene, and further characterized by canfene, sabinene, mircene, limonene, 1,8-cyneol, γ-terpinene, p-cimene and cariophylene.

Other details:

extraction yield: about 3.05% organoleptic characteristics: a clear yellow liquid with pleasant smell.

specific weight at 20°: 0.9037 refractive index: 1.4921 polarimetric deviation: 2.80 ester number: 14.0 additional applications: the drug is useful against cutaneous infection in sheep by *pseudomona aeruginosa*, since the propagation of the bacterium towards the fleece affects its quality, because it gets a lemon yellow color, and determines the wool that must be discarded, producing an important decrease in the wool world market.

It is also useful against puerperal pathologies like Septic Metrills because of primary and/or secondary reasons in bovine cattle, swine and herd of breeding mares that is caused by *pseudomona aeruginosa*, producing serious repercussions over the female fertility. Other human therapeutic application is noticed when the present drug is provided in fluid extract form, the menstruation is regularizod and/or the menopausic pathology is lightened in the case of amenorrhea and/or other irregularity conditions in the menstrual cycle.

The patient has shown *Pseudomona aeruginosa* culture development in the left ear for about a two year-term.

During this time, she was treated with antibiotics sensitive to the microorganism, but the results were negative.

At that step, the doctor used the usual topic application of acetic acid drops, diluted at 1% in alcohol vehicle at 95° C., with also negative results. In that situation, two drops of the dilution of the present drug in said ear was provided with the aforesaid formulation, three times a day for three days, with positive results, disappearing the *Pseudomona aeruginosa* without causing toxicity in the human cells.

The drug is at present used with glycerin USP as vehicle for the eradication of *Staphylococcus aureus* cultures in nose and throat. According to the exudate, a decrease of said microorganism concentration is noticed in a three day-term. The drug concentration can be increased or the therapeutical application the can be prolonged, because the over kill time is very long.

| BACTERICIDE ACTIVITY DETERMINATION | |
|---|---|
| Assay | |
| - Strains: | 1. *Staphylococcus aureus* ATCC 29737 |
| | 2. *Pseudomonas aeruginosa* ATCC 29366 |
| - Product concentration: 100% | |
| - Exposition time: 10 niinutes | |
| Results | |
| - Original bacterial concentration: | 1. $1.1 \times 10^6$ ufc/ml |
| | 2. $1.0 \times 10^6$ ufc/ml |
| - Final bacterial concentration: | 1. <1 ufc/ml |
| | 2. <1 ufc/ml |
| Conclusion: | |
| Efficiency: | 1. >99.9999% |
| | 2. >99.9999% |

After a quality and quantity determination through gaseous chromatography the sample is injected in a Carbowaz 20M capillar column (of 25 m, I.D. 0.22 mm, film 0.25 μm). The following compounds are determinated: α-pinene, canfene, β-pinene, mircene, α-phellandrene, limonene, cyneol, β-phellandrene, γ-terpinene, p-cimene, cariophylene and sabinene.

The entire signals represent the 78,6 % w/w of the essential oil.

ESSENTIAL OIL PREPARATION

Calculation Report

| CH₂ PKNO | TIME | AREA | HEIGHT | MK | IDNO | CONC | NAME |
|---|---|---|---|---|---|---|---|
| 1 | 7.206 | 15304 | 5385 | | | 1.1295 | |
| 2 | 7.476 | 192097 | 59980 | V | | 14.1779 | α-Pinene |
| 4 | 8.402 | 111388 | 34603 | V | | 8.2211 | Canfene |
| 5 | 9.385 | 140708 | 38490 | | | 10.3851 | β-Pinene |
| 6 | 9.706 | 215528 | 57322 | V | | 15.9072 | Sabinene |
| 7 | 10.724 | 61508 | 17056 | | | 4.5396 | Mircene |
| 8 | 10.876 | 70517 | 20516 | V | | 5.2046 | α-Phellandrene |
| 9 | 11.266 | 5771 | 1719 | V | | 0.4259 | |
| 10 | 11.902 | 241592 | 51516 | | | 17.8309 | Limonene |
| 11 | 12.189 | 44129 | 10356 | V | | 3.257 | 1-8 Cyneol + β-Phellandrene |
| 12 | 13.285 | 13170 | 3335 | | | 0.972 | γ-terpinene |
| 13 | 14.189 | 27374 | 8180 | | | 2.0203 | |
| 21 | 23.038 | 5674 | 1468 | V | | 0.4188 | |

-continued

| CH₂ PKNO | TIME | AREA | HEIGHT | MK | IDNO | CONC | NAME |
|---|---|---|---|---|---|---|---|
| 27 | 24.953 | 5214 | 1248 | V | | 0.3848 | |
| 28 | 25.065 | 7191 | 1799 | V | | 0.5307 | |
| 29 | 25.418 | 17828 | 4229 | V | | 1.3158 | Cariofilene |
| 30 | 25.710 | 24663 | 6282 | V | | 1.8203 | |
| 37 | 27.801 | 7101 | 1585 | V | | 0.5241 | |
| 38 | 28.286 | 5466 | 1128 | V | | 0.4034 | |
| 41 | 29.063 | 24068 | 5534 | V | | 1.7763 | 0.5241 |
| 43 | 29.391 | 10682 | 2475 | V | | 0.7884 | |
| 44 | 29.839 | 21919 | 5261 | V | | 1.6178 | |
| 45 | 30.465 | 37442 | 8709 | | | 2.7634 | |
| 46 | 30.585 | 12355 | 2961 | V | | 0.9119 | |
| 66 | 39.177 | 6460 | 1490 | | | 0.4768 | |
| 73 | 41.220 | 10577 | 2457 | V | | 0.7807 | |
| 75 | 42.370 | 12389 | 2734 | | | 0.9144 | |
| 79 | 44.139 | 6793 | 1299 | V | | 0.5014 | |
| TOTAL | | 1354906 | 359117 | | | 100 | |

TOTAL IDENTIFICATED: 78.6%

According to the pharmacological kinetic, the present drug at 1.5% dilution with glycerin in pharmaceutical degree USP as vehicle was provided over the following chart of clinical status:

a) Local symptoms: Presence of open, bleeding wounds with big suppuration in the external backpart of the right leg. A greenish yellow purulent running sore with fetid smell, small and medium vesicles with aqueous content of amber-like color. swelling, inflammation and color in the zone were noticed for five months.

b) General symptoms: High temperature, about 38.5° C., depression, light anorexy.

According to the bacteriological exudate, a great number of Pseudomonas aeruginosa colonies were noticed.

According to the antibiogram, Lazar Ciprofioxacine was prescribed and provided via oral, but improvement in health was not noticed.

According to the detailed kinetic, when the present drug was provided in topic form once a day, for ten days, an improvement in health was noticed on the second day. The temperature turns to normal temperature and the suppuration stops. A reepithelization in the zone was observed on the fifth day.

ANALYSIS OF THE LEG ULCER EXUDATE

Epithelial cells, small quantity of polynuclear cells and abundant quantity of negative-Gram bacillus were observed.

Culture

Development of abundant *Pseudomonas aeruginosa* colonies.

| Antibiogram: | |
|---|---|
| First line | |
| Gentamycin | sensitive |
| Second line | |
| Cefoperazone | intermediate |
| External use | |
| Neomycin | sensitive |
| Kanamycin | strong |
| Polymyxin B | sensitive |

I claim:

1. A pharmaceutical composition having bactericidal properties, which composition comprises a bactericidally effective amount of an essential oil extract distilled from a resinous tree *Schinus Molle L.* and a pharmaceutically acceptable carrier, said extract comprising α-phellandrene, β-phellandrene, carvacol, E-pinene, and β-pinene.

2. The pharmaceutical composition of claim 1 which further comprises canfene, sabinene, mircene, limonene, 1,8-cyneol, γ-terpinene, p-cimene and cariophylene.

3. The pharmaceutical composition of claim 1 wherein said pharmaceutically acceptable carrier is selected from the group consisting of ethyl alcohol, vaseline and glycerin.

4. The pharmaceutical composition of claim 1 wherein said pharmaceutically acceptable carrier is selected from the group consisting of ethyl alcohol, Vaseline and glycerin, and wherein said composition has bactericidal activity against *Pseudomonas aeruginosa*, *Staphylococcus aureus* and *Extreptococo*.

5. The pharmaceutical composition of claim 1 wherein said extract is further characterized as a clear yellow liquid with a specific weight at 2° C. of about 0.9, a refractive index of about 1.49, a polarimetric deviation of about 2.8 and an ester number of about 14.

6. The pharmaceutical composition of claim 1 wherein said extract is present in an amount of 0.5–2% w/v.

7. A method for treating infections of *Pseudomonas aeruginosa*, *Staphylococcus aureus* and *Extreptococo* in a human or animal patient, comprising applying a pharmaceutical composition to the patient's epidermis, which composition comprises a bactericidally effective amount of an essential oil extract distilled from a resinous tree *Schinus Molle L.* and a pharmaceutically acceptable carrier, wherein said extract comprises α-phellandrene, β-phellandrene, carvacol, α-pinene, and β-pinene.

8. The method of claim 7 wherein the composition is applied to a patient's ear, nose or throat.

9. The method of claim 7 wherein the composition is applied to an infected site or surgical incision.

10. The method of claim 7 wherein said composition contains said extract in an amount of 0.5–2% w/v.

* * * * *

UNITED STATES PATENT AND TRADEMARK OFFICE
CERTIFICATE OF CORRECTION

PATENT NO. : 5,635,184
DATED : June 3, 1997
INVENTOR(S) : Ricardo M. Camaño

It is certified that error appears in the above-indentified patent and that said Letters Patent is hereby corrected as shown below:

On the title page, the Inventor's name should read:
--[75]   Inventor: Ricardo M. Camaño--

Signed and Sealed this

Fourteenth Day of September, 1999

Attest:

Q. TODD DICKINSON

*Attesting Officer*          *Acting Commissioner of Patents and Trademarks*